United States Patent
Averous et al.

(10) Patent No.: US 9,675,395 B2
(45) Date of Patent: Jun. 13, 2017

(54) OSTEOSYNTHESIS CLIP

(71) Applicant: ADSM, Wettolsheim (FR)

(72) Inventors: Christophe Averous, Mittelhausbergen (FR); Christophe Cermolacce, Marseilles (FR); Patrice Determe, Toulouse (FR); Stephane Guillo, Bordeaux (FR); Hubert Rocher, Pessac (FR); Christophe Roy, Chatuzange le Goubet (FR); Jean-Charles Roussouly, Villeurbanne (FR); Arnaud Fiquet, Caluire (FR); Bertrand Seutin, La Batie Rolland (FR); Gualter Vaz, Lyons (FR)

(73) Assignee: ADSM, Wettolsheim (FR)

( * ) Notice: Subject to any disclaimer, the term of this patent is extended or adjusted under 35 U.S.C. 154(b) by 470 days.

(21) Appl. No.: 14/356,743

(22) PCT Filed: Nov. 6, 2012

(86) PCT No.: PCT/FR2012/052550
§ 371 (c)(1),
(2) Date: May 7, 2014

(87) PCT Pub. No.: WO2013/068682
PCT Pub. Date: May 16, 2013

(65) Prior Publication Data
US 2014/0309639 A1    Oct. 16, 2014

(30) Foreign Application Priority Data

Nov. 7, 2011 (FR) .................... 11 60097

(51) Int. Cl.
*A61B 17/84* (2006.01)
*A61B 17/064* (2006.01)
*A61B 17/80* (2006.01)

(52) U.S. Cl.
CPC ........ *A61B 17/846* (2013.01); *A61B 17/0642* (2013.01); *A61B 17/0643* (2013.01); *A61B 17/0644* (2013.01); *A61B 17/8004* (2013.01)

(58) Field of Classification Search
CPC .............. A61B 17/064; A61B 17/0642; A61B 17/0643; A61B 17/0644; A61B 2017/0641; A61B 2017/0645; A61B 2017/0646
(Continued)

(56) References Cited

U.S. PATENT DOCUMENTS 3,862,631 A * 1/1975 Austin ............... A61B 17/0642
606/212
4,444,181 A * 4/1984 Wevers .............. A61B 17/0642
606/75
(Continued)

FOREIGN PATENT DOCUMENTS

EP    0852128 A1    7/1998
EP    1504723 A2    2/2005
(Continued)

OTHER PUBLICATIONS

International Search Report for corresponding International PCT Application No. PCT/FR2012/052550, mailed Apr. 16, 2013.

*Primary Examiner* — Christian Sevilla
*Assistant Examiner* — Eric S Gibson
(74) *Attorney, Agent, or Firm* — Workman Nydegger (57) ABSTRACT

An osteosynthesis clip having an overall U-shape, comprising two anchor bars and a connecting bar. The connecting bar including a longitudinal opening adapted to assume a closed configuration and an open configuration. The clip comprises a compression piece having a broadly oval-shaped section, housed in the opening. The piece is adapted to be rotated within the opening, thus causing the opening to (Continued)

shift from its closed configuration to at least one the open configuration and vice versa.

11 Claims, 3 Drawing Sheets

(58) Field of Classification Search
USPC .......................................... 606/75; 227/902
See application file for complete search history.

(56) References Cited

U.S. PATENT DOCUMENTS

| | | | |
|---|---|---|---|
| 4,454,875 A * | 6/1984 | Pratt | F16B 15/02 606/219 |
| 4,723,540 A * | 2/1988 | Gilmer, Jr. | A61B 17/0642 411/456 |
| 4,887,601 A | 12/1989 | Richards | |
| 4,994,063 A * | 2/1991 | Garner | A61B 17/0642 606/75 |
| 5,053,038 A * | 10/1991 | Sheehan | A61B 17/0642 606/75 |
| 5,352,229 A * | 10/1994 | Goble | A61B 17/0642 606/220 |
| 5,449,359 A * | 9/1995 | Groiso | A61B 17/0642 411/459 |
| 5,662,655 A * | 9/1997 | Laboureau | A61B 17/0642 606/297 |
| 5,779,707 A * | 7/1998 | Bertholet | A61B 17/8004 606/301 |
| 5,782,865 A * | 7/1998 | Grotz | A61B 17/0401 606/104 |
| 5,947,999 A * | 9/1999 | Groiso | A61B 17/0642 606/216 |
| 5,993,476 A | 11/1999 | Groiso | |
| 6,197,042 B1 * | 3/2001 | Ginn | A61B 17/0057 606/139 |
| 6,325,805 B1 * | 12/2001 | Ogilvie | A61B 17/0642 606/300 |
| 7,635,367 B2 | 12/2009 | Groiso | |
| 8,211,109 B2 | 7/2012 | Groiso | |
| 8,372,075 B2 | 2/2013 | Groiso | |
| 8,728,120 B2 * | 5/2014 | Blier | A61B 17/0644 227/902 |
| 8,900,281 B2 * | 12/2014 | Reisberg | A61B 17/8076 606/283 |
| 2002/0007182 A1 * | 1/2002 | Kim | A61F 2/0811 606/53 |
| 2002/0029064 A1 * | 3/2002 | Kanner | A61B 17/0057 606/221 |
| 2003/0032981 A1 * | 2/2003 | Kanner | A61B 17/0057 606/219 |
| 2003/0139746 A1 * | 7/2003 | Groiso | A61B 17/0642 606/75 |
| 2004/0093024 A1 * | 5/2004 | Lousararian | A61B 17/0057 606/213 |
| 2005/0049600 A1 | 3/2005 | Groiso | |
| 2005/0055027 A1 * | 3/2005 | Yeung | A61B 17/0401 606/75 |
| 2005/0273108 A1 | 12/2005 | Groiso | |
| 2006/0142771 A1 * | 6/2006 | Beutter | A61B 17/0642 606/75 |
| 2006/0167459 A1 * | 7/2006 | Groiso | A61B 17/0642 606/248 |
| 2006/0287674 A1 * | 12/2006 | Ginn | A61B 17/0057 606/221 |
| 2008/0077144 A1 | 3/2008 | Crofford | |
| 2008/0167666 A1 | 7/2008 | Fiere et al. | |
| 2008/0319443 A1 * | 12/2008 | Focht | A61B 17/0642 606/75 |
| 2010/0042160 A1 | 2/2010 | Biyani et al. | |
| 2010/0082030 A1 | 4/2010 | Groiso | |
| 2010/0087822 A1 | 4/2010 | Groiso | |
| 2010/0241161 A1 * | 9/2010 | Heftman | A61B 17/0643 606/213 |
| 2011/0118842 A1 * | 5/2011 | Bernard | A61B 17/0642 623/17.11 |
| 2011/0160766 A1 * | 6/2011 | Hendren | A61B 17/0487 606/232 |
| 2013/0030438 A1 * | 1/2013 | Fox | A61B 17/0642 606/75 |
| 2014/0276830 A1 * | 9/2014 | Cheney | A61B 17/0642 606/75 |
| 2015/0313592 A1 * | 11/2015 | Coillard-Lavirotte | A61B 17/0642 606/75 |

FOREIGN PATENT DOCUMENTS

| | | |
|---|---|---|
| FR | 2622430 A1 | 5/1989 |
| WO | 8904146 A1 | 5/1989 |
| WO | 2006120551 A1 | 11/2006 |

* cited by examiner

OSTEOSYNTHESIS CLIP

BACKGROUND

The present invention relates to an osteosynthesis clip used, for example, to perform osteotomies, arthrodesis between two bone fragments, or fix soft tissues to the bone.

SUMMARY

There exist several surgical clips for bone repair. Some of these clips have an overall U shape, the distal ends of the vertical U-shaped bars being intended to be inserted into two different bone fragments, in order to bring them close together for example.

In the present application, the distal end of a device, such as an implant or a clip, is to be understood as meaning the end farthest away from the surgeon's hand and the proximal end is to be understood as meaning the end nearest the surgeon's hand. Similarly, in this application, the "distal direction" is to be understood as meaning the impaction direction of the clip and the "proximal direction" is to be understood as meaning the opposite direction from the impaction direction.

In general, prior to the installation of a U-shaped clip, two holes are drilled, one in each of the two bone fragments intended to be brought together, and then the clip is impacted, with each vertical bar inserted in a hole. Once the clip is impacted, it is very difficult to adjust the compression exerted by the two vertical bars: thus, if this compression is too low, bringing the two bone fragments close together will not be optimal. Similarly, if this compression is too high, there is no way to release this pressure.

There is therefore the need for an overall U-shaped clip enabling to adjust the compression exerted by the two vertical bars of the U shape, for example on two bone fragments to be brought close together, in particular once the clip has been impacted, that is to say, once it has been preinstalled with the two vertical bars of the U shape already inserted into the bone fragments.

The present invention aims to address this need by providing an overall U-shaped clip whereof the compression exerted by the two vertical bars of the U shape may be increased or reduced after impaction of the clip.

The present invention relates to an overall U-shaped osteosynthesis clip, comprising:
  at least two anchor bars corresponding to the two vertical bars of the U shape, each anchor bar comprising a distal end, intended to be inserted into a bone element, and a proximal end, and
  at least one connecting bar, corresponding to the horizontal bar of the U shape, connecting together the respective proximal ends of the two anchor bars, said connecting bar comprising at least one longitudinal opening splitting it into two opposite side walls connected together at the ends thereof, deformable in the plane P containing the connecting bar and perpendicular to the plane containing the U-shaped clip, such that the opening is adapted to assume a closed configuration, in which the two anchor bars are substantially parallel to each other and said two side walls are brought close to each other such that the distance between the two proximal ends of the two anchor bars has a value L1, and at least an open configuration, in which the central regions of said two side walls are spaced apart from each other on either side of said opening, and the distance between the two proximal ends of the two anchor bars has a value L2 strictly lower than L1, characterized in that
said clip further comprises a compression piece having at least one portion called active portion, the cross-section of which in a plane A of said piece has an overall oval shape, said piece being housed within said opening with its plane A coinciding with said plane P and at least one part of the outer face of its active portion in contact with at least one part of the inner faces of said two side walls of the connecting bar, said piece being adapted to undergo a rotation about an axis B passing through the center of said oval shape of said active portion and perpendicular to said plane P, thus causing said opening to move from its closed configuration to at least one so-called open configuration, and vice versa.

Thus, in the clip according to the invention, the distance between the two proximal ends of the two anchor bars may vary between L1 and L2 thanks to the rotation of the compression piece housed in the opening made in the connecting bar. Indeed, this compression piece having an overall oval shape in its plane A, its rotation in the plane P deforms the side walls by forcing them to move away from each other, thereby causing the opening made in the connecting bar to vary in width and the two proximal ends of the two anchor bars to move closer to each other.

For the purposes of the present application, by "overall oval" is meant an oval, elliptical, oblong or ovoid shape, or more generally any form other than a disc or circle inscribed in an oval, having an axis of revolution, but the radius of which is not constant.

Since it is housed in said opening, said piece remains accessible to the user, for example a surgeon, even when the two anchor bars have been inserted into the bone elements, or other organs, which the anchor bars are intended to bring close together. Thus, the surgeon may, if necessary by means of a suitable tool, impart to said piece a rotational movement to vary the distance between the two proximal ends of the two anchor bars.

By varying the distance between the two proximal ends of the two anchor bars, the distance between the two anchor bars is also varied and the compression exerted by the two anchor bars on the bone elements or organs in which they are inserted through the distal ends thereof is thereby varied.

The clip according to the invention makes it possible to maintain the bone elements in a normal physiological position after surgery and a compression for the duration of bone consolidation.

For example, one or more clips according to the invention may be used in the treatment of hallux rigidus: after revival of the articular surfaces, these are maintained in close contact by means of one or more clips according to the invention, for the duration of consolidation.

The clip according to the invention may thus be used to bring close together bone fragments of the foot or hand or any other member or to perform an arthrodesis of a joint. The clip according to the invention may also be used to bring close together two adjacent vertebrae.

In one embodiment, the clip according to the invention comprises means for guiding the rotation of said piece in said plane P. For example, the guiding means comprise at least one groove and one bead adapted to engage one inside the other to guide the rotation of said piece in said plane P, one of said groove and said bead being located on the inner faces of said side walls, the other among said groove and said bead being located on said outer face of said active portion of said piece. For example, the inner face of each side wall may comprise a groove, located in the plane P, and the outer face of the active portion of the compression piece includes a peripheral bead, also located in the plane P, such that the bead is engaged in the groove of each one of the two side walls: thus, when the compression piece rotates about its axis B, the bead remains engaged in the two grooves, ensuring that the active portion of the compression piece remains in the plane P, thus causing the two side walls to move away from each other or to get closer to each other. In another embodiment, the inner face of each side wall may comprise a bead, located in the plane P, and the outer face of the active portion of the compression piece includes a peripheral groove, also located in the plane P, such that the peripheral groove is engaged in the bead of each one of the two side walls.

In one embodiment, the clip according to the invention comprises means for blocking said piece at different angles of rotation. For example, the blocking means comprise a plurality of reliefs distributed along the periphery of said active portion, adapted to successively engage in one or more complementary reliefs located on the inner faces of said side walls, the engagement of one or more reliefs in the complementary relief(s) blocking said rotating piece at a determined angle of rotation. The active portion of the compression piece having an overall oval shape, this embodiment makes it possible to select a preferred width for the opening and thus adjust the preferred distance between the proximal ends of the two anchor bars, and therefore the compression force exerted by these two anchor bars on the bone elements or other organs in which they are inserted. Indeed, the plurality of reliefs distributed over the periphery of the active portion makes it possible to choose between several possible widths for the opening, which may be blocked by engagement of a relief in the complementary relief.

In one embodiment, the clip according to the invention comprises misalignment means for misaligning said anchor bars, arranged to cause the respective distal regions of said anchor bars to alternately move away from each other or get closer to each other, in an open configuration of said opening. For example, said misalignment means comprise a longitudinal slot made in each side wall and splitting said wall into two longitudinal sections, a proximal section and a distal section, connected together by their ends, each of said proximal and distal sections being deformable in the plane P, independently of the other section.

Thus, in one embodiment of the invention, said part of said outer face of said active portion of said piece being in contact only with the inner faces of said proximal sections of said side walls, said distal regions of said two anchor bars move away from each other when said opening is in an open configuration.

In another embodiment of the invention, said part of said outer face of said active portion of said piece being in contact only with the inner faces of said distal sections of said side walls, said distal regions of said two anchor bars get closer to each other when said opening is in an open configuration. This embodiment makes it possible to further reinforce the compression exerted by the anchor bars on the bone elements, or other organs, in order to bring them close together.

In one embodiment of the invention, the distal regions of said two anchor bars are provided with hooking notches intended to reinforce anchoring of said anchor bars into the bone elements.

In one embodiment of the invention, the proximal face of said piece includes a surface adapted to cooperate with a tool in order to transmit a rotational movement to said piece. For example, said surface has a recess having a hexagonal profile, said recess being adapted to accommodate a key of corresponding profile enabling to rotate the compression piece within the opening in which it is housed.

BRIEF DESCRIPTION OF THE DRAWINGS

The advantages of the present invention will be seen more clearly from the following description and the accompanying drawings wherein.

DETAILED DESCRIPTION OF VARIOUS EMBODIMENTS

Figure 1:
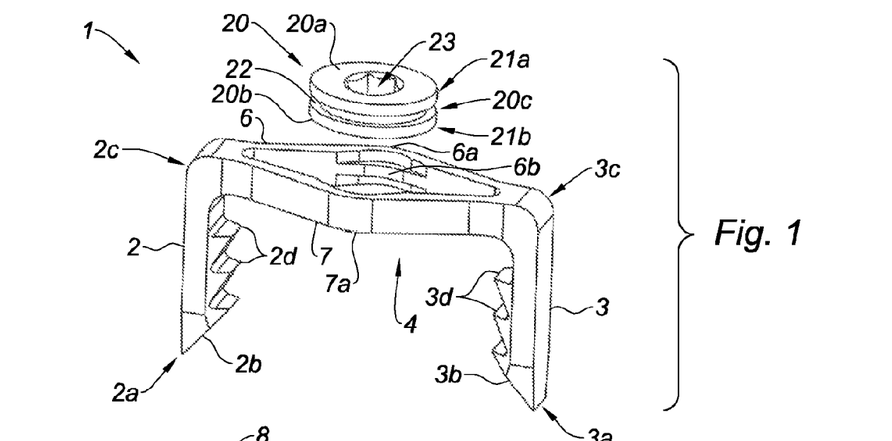
FIG. 1 is an exploded perspective view of a clip according to the invention.
Figure 2:
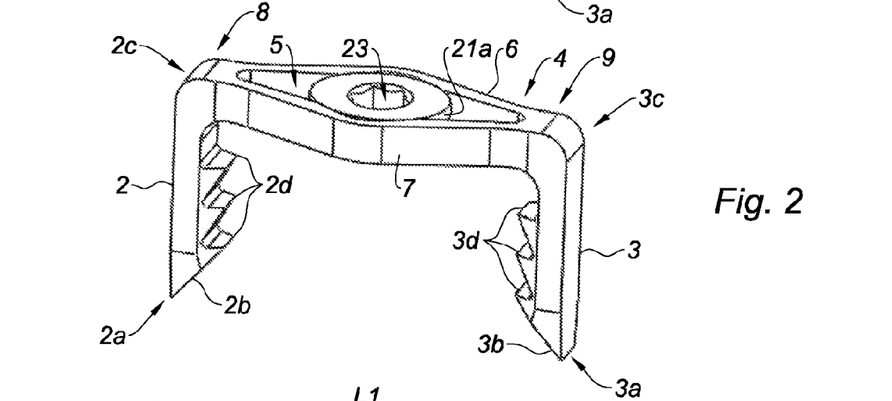
FIG. 2 is a perspective view of the clip in FIG. 1 with the compression piece housed in the opening.
Figure 8:
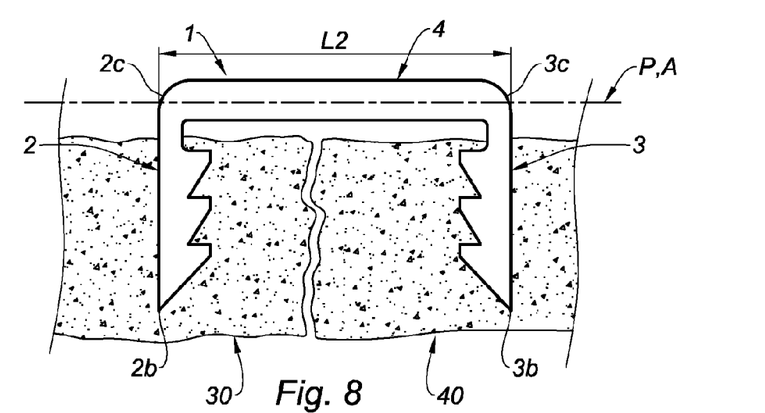
FIG. 8 is a sectional view of the clip in FIG. 1 when implanted, with the opening in an open configuration, bringing two bone elements close together.

Referring to FIGS. 1 and 2, a clip 1 according to the invention is shown, used for example to bring two bone fragments close together (see FIG. 8). The bone fragments may be bone fragments of the foot or the hand, or two adjacent vertebrae to be brought close together. The clip 1 has an overall U shape and is generally comprised within the plane of the U shape, also called plane of the clip 1.

The clip 1 comprises two anchor bars (2, 3) corresponding to the vertical bars of the U shape. Each anchor bar (2, 3) comprises a distal end (2a, 3a) intended to be inserted into a bone fragment. As shown in these figures, the distal ends (2a, 3a) of the anchor bars (2, 3) have a pointed portion (2b, 3b) to facilitate penetration of the anchor bars (2, 3) into the bone fragments. Each anchor bar (2, 3) also has a proximal end (2c, 3c) located opposite the distal end (2a, 3a).

In addition, each anchor bar (2, 3) has, in its distal region, a plurality—three in the example shown—of notches (2d, 3d) intended to reinforce anchoring of each bar (2, 3) into the bone fragment and to limit movement of the clip 1 in the proximal direction once the latter is inserted into the bone fragments to be brought close together.

The clip 1 further includes a connecting bar 4, corresponding to the horizontal bar of the U shape and connecting together the respective proximal ends (2c, 3c) of the two anchor bars (2, 3). As can be seen in the figures, the two anchor bars (2, 3) and the connecting bar 4 are located in the same plane, the plane of the U shape. In this plane, the anchor bars (2, 3) are substantially parallel to each other.

The connecting bar 4 includes a longitudinal opening 5 splitting it into two opposite side walls (6, 7), connected together through the ends thereof: these ends correspond to the junction points (8, 9) of the connecting bar 4 with the anchor bars (2, 3).

Figure 3:
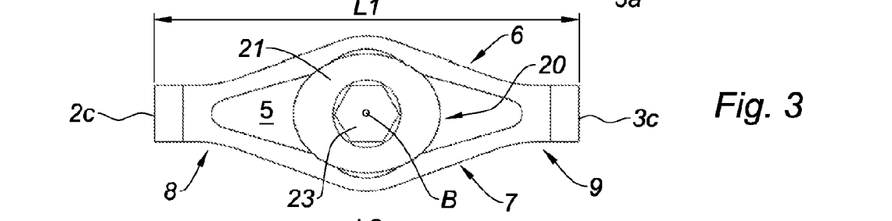
FIG. 3 is a top view of the clip in FIG. 2 in the closed configuration of the opening.
Figure 4:
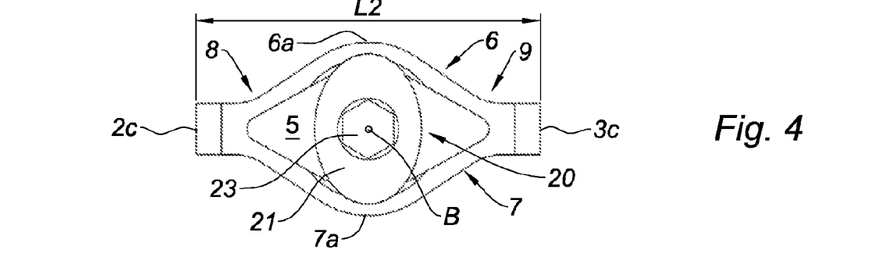
FIG. 4 is a top view of the clip in FIG. 2 in an open configuration of the opening.

Referring to FIGS. 3 and 4, the side walls (6, 7) are deformable in the plane P; the plane P, shown in FIG. 8, being the plane containing the connecting bar 4 and perpendicular to the plane containing the U-shaped clip. As can be seen in these figures, the opening 5 is adapted to assume a closed configuration (FIG. 3), in which the two anchor bars (2, 3) are substantially parallel to each other and said two side walls (6, 7) are brought close together such that the distance between the two proximal ends (2c, 3c) of the two anchor bars (2, 3) has a value L1, and at least an open configuration (FIG. 4), in which the central regions (6a, 7a) of said two side walls (6, 7) are spaced apart from each other on either side of said opening 5, and the distance between the two proximal ends (2c, 3c) of the two anchor bars (2, 3) has a value L2 strictly lower than L1.

As shown in FIG. 1, the inner face of the central region 6a of the side wall 6 is provided with a bead 6b. Although not shown in the figure, the inner face of the central region 7a of the side wall 7 is provided with a bead 7b, identical to the bead of the opposite side wall.

For example, the connecting bar 4 and the anchor bars (2, 3) of the clip 1 are made of a material selected from among stainless steel, chromium/cobalt alloys, polylactic acid, polyetheretherketone, titanium, and mixtures thereof.

The clip further includes a compression piece 20 in the form of a chip having the shape of a cylinder with an oval cross-section: thus, the compression piece 20 has two opposite faces of oval section, a proximal face 20a and a distal face 20b, and a peripheral wall 20c connecting the two proximal 20a and distal 20b faces. The cylinder height being much smaller than the dimensions (width and length) of the opposite faces, the compression piece is broadly comprised within a plane A (chip plane) and comprises an axis B of rotation passing through the center of each one of the faces having oval section, and perpendicular to this plane A of the compression piece. In the example shown in FIGS. 1-4, the peripheral wall 20c of the compression piece 20 is provided, at mid-height, with a peripheral groove 22: this peripheral groove 22 thus splits the peripheral wall 20c into a proximal peripheral part 21a and a distal peripheral part 21b. As can be seen in the figures, the peripheral proximal 21a and distal 21b parts of the compression piece 20 have, in the plane of said piece, an overall oval-shaped section. These peripheral proximal 21a and distal 21b parts of the compression piece together form a portion called active portion (21a, 21b) of the compression piece 20, which, as will be seen from the following description, is intended to cooperate with the inner faces of the side walls (6, 7) in order to move the opening 5 from its closed configuration to an open configuration.

In the example shown, the proximal face 20a of the compression piece 20 is provided with a recess 23 of hexagonal cross-section: as will be seen in the following description, this recess 23 is adapted to accommodate a key of complementary shape in order to impart a rotational movement to the compression piece.

The compression piece 20 can be made of a material selected from among stainless steel, chromium/cobalt alloys, polylactic acid, polyetheretherketone, titanium, and mixtures thereof.

The use of the clip 1 for example to bring two bone fragments close together will now be described with reference to FIGS. 1-4 and 8.

The clip 1 is supplied to the surgeon in its assembled position as shown in FIGS. 2 and 3, in the closed configuration of the opening 5. In this position, the compression piece 20 has been snapped into the opening 5 such that its active portion (21a, 21b) is in the plane P of the connecting bar 4, and the beads (6b, 7b) of the inner faces of the side walls (6, 7) are engaged in the groove 22 of the peripheral wall of the compression piece 20. Furthermore, in this closed configuration of the opening 5, the major axis of the compression piece 20 is aligned on the longitudinal axis of the connecting bar 4. The active portion (21a, 21b) of the compression piece 20, namely the peripheral proximal 21a and distal 21b portions, are in contact with the inner faces of the side walls (6, 7). The anchor bars (2, 3) are substantially parallel to each other in the plane of the clip 1, i.e. in the plane of the U shape formed by the clip 1.

As can be seen in FIG. 3, in the closed configuration of the opening 5, the side walls (6, 7) are brought close to each other such that the distance between the two proximal ends (2c, 3c) of the two anchor bars (2, 3) has a value L1.

To perform an osteosynthesis, or bringing two bone fragments close together, for example, a first bone fragment 30 and a second bone fragment 40 as shown in FIG. 8, the surgeon grasps, by means of an appropriate ancillary (not shown), the clip 1 in the closed configuration of the opening 5 as shown in FIG. 2, and he impacts the clip 1 by inserting the two anchor bars (2, 3) from the pointed portions (2b, 3b) of their distal ends (2a, 3a) in two holes previously formed in the bone fragments (30, 40) to be brought close together.

Once the clip 1 is thus inserted, the surgeon seizes a tool (not shown) having a key having a shape complementary to the recess 23, and imparts to the compression piece 20 a rotation about its axis B within the opening 5. During this rotation, the groove 22 of the compression piece 20 and the beads (6b, 7b) of the inner faces of the side walls (6, 7) are used as guiding means, ensuring that the rotation of the compression piece 20 does occur in the plane P containing the connecting bar 4 and perpendicular to the plane of the clip 1. Moreover, the active portion (21a, 21b) of the compression piece 20 being oval-shaped and in contact with the inner faces of the side walls (6, 7), rotation of the compression piece 20 causes the deformation of the side walls (6, 7) which move away from each other, as shown in FIG. 4. Movement of the central regions (6a, 7a) of the side walls away from each other causes the proximal ends (2c, 3c) of the anchor bars (2, 3) to get close to each other, and the distance between the two proximal ends (2c, 3c) has now a value L2 strictly lower than L1, as shown in FIG. 4.

Thus, rotation of the compression piece 20, once the anchor bars (2, 3) have been inserted into the bone fragments (30, 40) to be brought close together, makes it possible to adjust and, in particular, to increase the compression exerted by the two anchor bars (2, 3) on said bone fragments (30, 40).

In FIG. 8, the clip 1 is shown when inserted into the bone fragments (30, 40) and after rotation of the compression piece 20 as described above: the distance between the two proximal ends (2c, 3c) of the anchor bars (2, 3) is therefore L2, i.e., this distance is less than the distance L1 of the step of clip 1 impaction. The two bone fragments (30, 40) have therefore been brought close to each other by rotation of the compression piece 20.

In the example shown in FIG. 8, the two anchor bars (2, 3) are also parallel to each other in the plane of the clip 1 when the opening 5 is in an open configuration, that is to say, when the clip 1 is implanted into the bone fragments (30, 40) and the compression piece 20 has undergone the rotation described above. Indeed, in this example, the active portion (21a, 21b) of the compression piece 20 acting evenly over the entire height of the side walls (6, 7), movement of the proximal ends (2c, 3c) of the anchor bars (2, 3) close to each other is accompanied by a parallel movement of the anchor bars (2, 3) close to each other within the bone fragments.

The compression piece 20 makes it possible to securely fix the two bone fragments and prevent any movement inducing a displacement of the assembly or loss of compression.

Furthermore, the presence of the compression piece 20, which remains integral with the clip 1 once the latter has been implanted, makes it possible to prevent distension of the clip and maintain the opening 5 in a permanently open configuration and thus preserve the desired compression on the two bone fragments (30, 40) in order to maintain them in a close-together position until bone fusion takes place.

In addition, the permanent presence of the compression piece 20, which is pressed against the bone fragments (30, 40), makes it also possible to prevent overlapping of these bone fragments.

Figure 5:
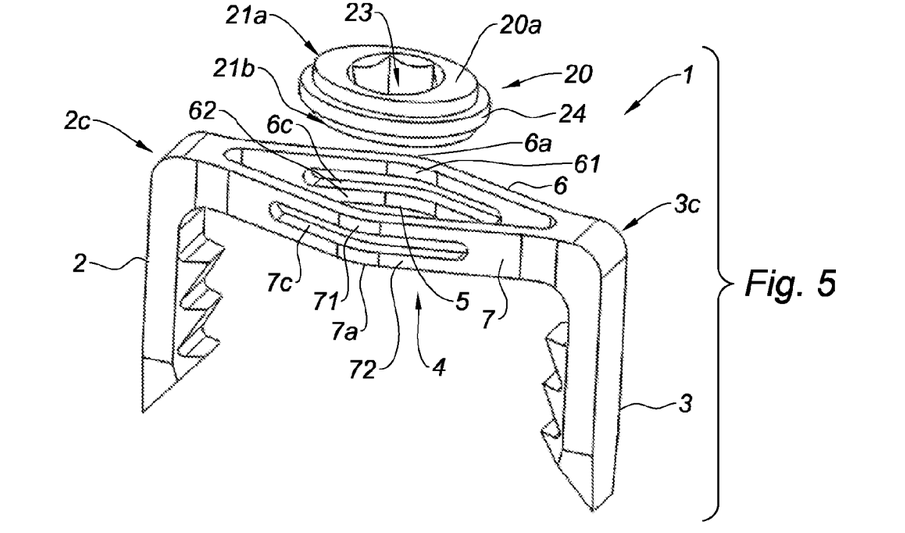
FIG. 5 is an exploded perspective view of a first alternative embodiment of the clip according to the invention.

Referring to FIG. 5, an alternative embodiment of the clip 1 of FIG. 1 is shown, wherein the groove and the beads of the means for guiding rotation of the compression piece 20 have been switched between the peripheral wall 20c of the compression piece 20 and the inner faces of the side walls (6, 7) of the connecting bar 4, the groove being a through groove and forming a slot. In this FIG. 5, the reference numerals denoting the same elements as in FIGS. 1-4 have been preserved.

The peripheral wall 20c of the compression piece 20 is thus provided with a peripheral bead 24 and the inner faces of the central regions (6a, 7a) of the side walls (6, 7) are each provided with a longitudinal slot (6c, 7c). The peripheral bead 24 is located at mid-height of the peripheral wall 20c and determines a peripheral proximal part 21a and a peripheral distal part 21b of the compression piece 20, which together form the active portion (21a, 21b) of the compression piece 20.

Moreover, the longitudinal slot 6c splits the side wall 6 into two longitudinal sections, a proximal section 61 and a distal section 62, connected together through their ends, each of said proximal 61 and distal 62 sections being deformable in the plane P independently of the other section, as will be seen later in the following description. Similarly, the longitudinal slot 7c splits the side wall into two longitudinal sections, a proximal section 71 and a distal section 72, connected together through their ends, each of said proximal 71 and distal 72 sections being deformable in the plane P independently of the other section.

When the clip 1 of FIG. 5 is in its assembled form, and the compression piece 20 is snapped into the opening 5, the peripheral bead 24 is engaged in the grooves (6c, 7c) of the two side walls (6, 7) and the active portion (21a, 21b) of the compression piece 20 is in contact with the inner faces of the side walls (6, 7): the peripheral bead 24 and the grooves (6c, 7c) act as means for guiding rotation of the compression piece 20 about its axis B and ensure that this rotation does occur in the plane P. The clip 1 of FIG. 5 may be used to bring two bone elements close together as described above for the clip of FIGS. 1-4.

Figure 6:
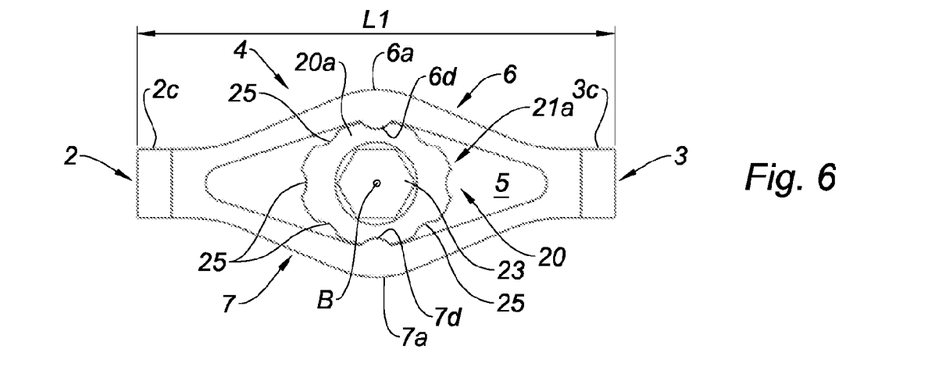
FIG. 6 is a top view of a second alternative embodiment of the clip according to the invention in the closed configuration of the opening.
Figure 7:
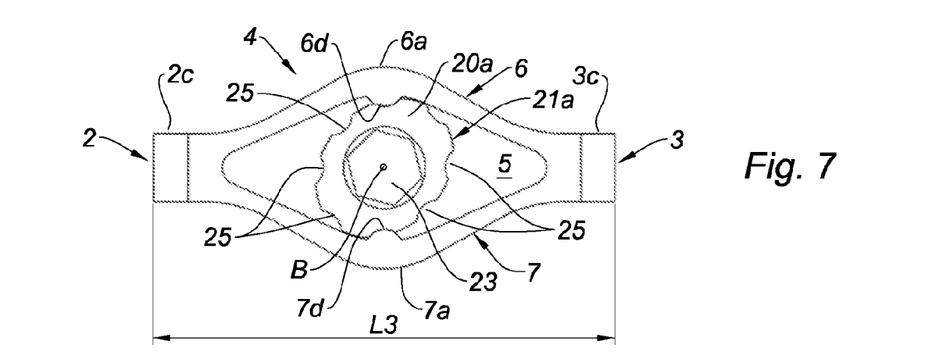
FIG. 7 is a top view of the clip in FIG. 6 in a blocked open configuration of the opening.

Referring to FIGS. 6 and 7, another alternative embodiment of the clip 1 of FIG. 1-4 or 5 is shown, further comprising means for blocking the compression piece 20 at different angles of rotation. In these figures, the reference numerals denoting the same elements as in FIGS. 1-4 have been preserved.

In this alternative embodiment of the clip 1 according to the invention, the active portion (only the peripheral proximal part 21a of which is shown in the figures) of the compression piece 20 is provided with a plurality of reliefs, for example in the form of notches 25, distributed along the periphery of said active portion 21a. The inner faces of the central regions (6a, 7a) of the side walls (6, 7) are each provided with a complementary relief, for example in the form of a lug (6d, 7d) adapted to interlock in one of the notches 25 in order to block the rotation of the compression piece 20. Due to the oval shape of the active portion 21a, it is thus possible to provide to the opening 5 several open configurations, with an opening width that may vary: the greater opening width being achieved when the major axis of the active portion 21 is perpendicular to the longitudinal axis of the connecting bar 4. In the example shown in FIG. 7, the opening is in a semi-open configuration, the major axis of the active portion 21a forming approximately an angle of 45° with the longitudinal axis of the connecting bar 4.

Thus, in accordance with the definitions given for the clip 1 of FIGS. 1-4, the distance between the two proximal ends (2c, 3c) in FIG. 7 has a value L3 of between L1 and L2. Such an embodiment of the clip 1 makes it thus possible to adjust the compression force exerted by the anchor bars (2, 3) on the bone elements to be brought close together, between a minimum compression, exerted when the opening 5 is in its closed configuration, as shown in FIG. 6, and a maximum compression, exerted when the opening is in its open configuration, with the major axis of the active portion 21a perpendicular to the longitudinal axis of the connecting bar 4.

Blocking the compression piece 20 at a certain angle of rotation may be temporary or permanent depending on the surgeon's wishes. The latter may, if he desires it, change the blocking angle by means of a tool provided with a key as described above and release the compression piece 20 to make it pivot up to a different angle of rotation.

Referring to FIGS. 9A to 10B, two alternative embodiments of a clip 1 similar to the one in FIG. 5 are shown, further comprising means for misaligning the anchor bars, arranged to alternately cause the respective distal regions of the two anchor bars to move away from each other or get close to each other, in an open configuration of the opening. In these figures, the U-shaped part of the clip, namely the anchor bars and the connecting bar, differs from the one in FIG. 5 only by the absence of notches (2d, 3d) for hooking the anchor bars (2, 3), and the reference numerals denoting the same elements as in FIG. 5 have been preserved.

Figure 9A:
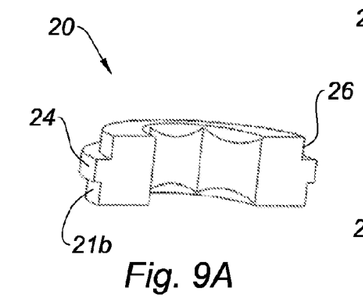
FIG. 9A is a perspective and sectional view of a compression piece usable with the U-shaped part of a clip similar to the one in FIG. 5, in order to make the distal regions of the anchor bars move closer to each other in an open configuration of the opening.

Referring to FIG. 9A, an alternative embodiment of the compression piece 20 in FIG. 5 is shown wherein the part of the compression piece 20 located proximally to the peripheral bead 24 is sized so as not to be in contact with the inner faces of the side walls (6, 7) of the connecting bar 4 when the compression piece 20 is housed within the opening 5, irrespective of the configuration of the opening 5. In particular, this proximal part of the compression piece 20, in the form of a ring 26 in the example shown in FIG. 9A, is sized so as not to cooperate with the proximal sections (61, 71) of the side walls (6, 7) (see FIG. 5). Thus, the ring 26 has an outer diameter smaller than the diameter of the opening 5 and it is not therefore part of the active portion of the compression piece 20: the active portion of the compression piece 20 of FIG. 9A is limited to the distal peripheral part 21b.

Figure 9B:
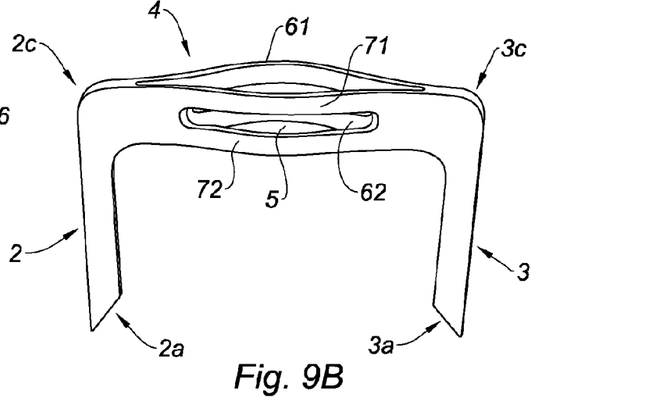
FIG. 9B is a perspective view of the U-shaped part of the clip usable with the compression piece in FIG. 9A, in an open configuration of the opening; however, in FIG. 9B, for the sake of clarity, the compression piece is not shown.

Accordingly, when the compression piece 20 in FIG. 9A is housed within the opening 5 of the U-shaped part of the clip in FIG. 5, and the compression piece 20 is submitted to a rotation as explained above, only the distal sections (62, 72) of the side walls (6, 7) are deformed, as shown in FIG. 9B: in this figure, for the sake of clarity, the compression piece 20 is not shown, but the deformation shown is the one caused by its presence. As can be seen in FIG. 9B, the deformation of the distal sections (62, 72), coupled with the non-deformation or very low deformation of the proximal sections (61, 71) causes, on the one hand, the proximal ends (2c, 3c) of the anchor bars, as already seen for FIG. 4, and on the other hand, the distal regions, particularly the distal ends (2a, 3a) of the two anchor bars (2, 3) to move close to each other, in an open configuration of the opening 5. Thus, this embodiment, as shown in FIGS. 9A and 9B, makes it possible to further increase the compression force exerted by the two anchor bars (2, 3) on two bone elements to be brought close together.

Figure 10A:
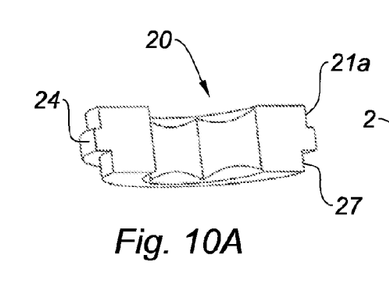
FIG. 10A is a perspective and sectional view of a compression piece usable with the U-shaped part of a clip similar to the one in FIG. 5, in order to move the distal regions of the anchor bars away from each other in an open configuration of the opening.

Referring to FIG. 10A, an alternative embodiment of the compression piece 20 in FIG. 5 is shown wherein the part of the compression piece 20 located distally to the peripheral bead 24 is sized so as not to be in contact with the inner faces of the side walls (6, 7) of the connecting bar 4 when the compression piece 20 is housed within the opening 5, irrespective of the configuration of the opening 5. In particular, this distal part of the compression piece 20, in the form of a ring 27 in the example shown in FIG. 10A, is sized so as not to cooperate with the distal sections (62, 72) of the side walls (6, 7) (see FIG. 5). Thus, the ring 27 has an outer diameter smaller than the diameter of the opening 5 and it is not part of the active portion of the compression piece 20: the active portion of the compression piece 20 in FIG. 10A is limited to the proximal peripheral part 21a.

Figure 10B:
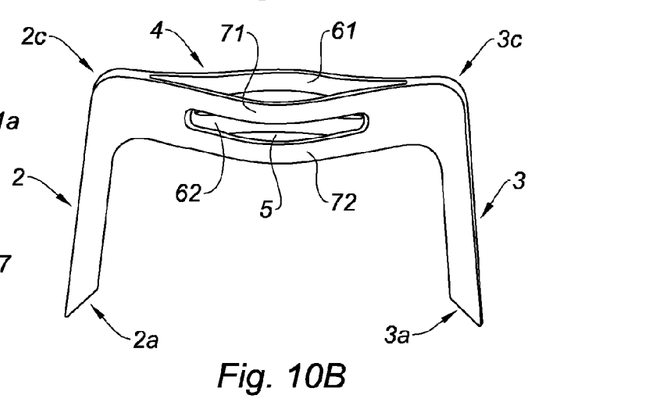
FIG. 10B is a perspective view of the U-shaped part of the clip usable with the compression piece in FIG. 10A, in an open configuration of the opening; however, in FIG. 10B, for the sake of clarity, the compression piece is not shown.

Accordingly, when the compression piece 20 in FIG. 10A is housed within the opening 5 of the U-shaped part of the clip in FIG. 5, and the compression piece 20 is submitted to a rotation as explained above, only the proximal sections (61, 71) of the side walls (6, 7) are deformed, as shown in FIG. 10B: in this figure, for the sake of clarity, the compression piece 20 is not shown, but the deformation shown is the one caused by its presence. As can be seen in this FIG. 10B, the deformation of the proximal sections (61, 71) coupled with the non-deformation or very low deformation of the distal sections (62, 72), causes, on the one hand, the proximal ends (2c, 3c) of the anchor bars to move close to each other, as seen for FIG. 4, and causes, on the other hand, the distal regions, particularly the distal ends (2a, 3a) of the two anchor bars (2, 3) to move away from each other, in an open configuration of the opening 5. Thus, this embodiment makes it possible to reduce the compression force exerted by the two anchor bars (2, 3) on two bone elements to be brought together.

The clip according to the invention makes it possible to vary the compression exerted on two bone fragments to be brought close together after impaction of the clip, for example by increasing or reducing this compression. It further makes it possible to maintain the compression force selected for the required duration of the bone consolidation.

The invention claimed is:

1. An osteosynthesis clip having an overall U-shape, comprising:
   at least two anchor bars corresponding to two vertical bars of the U shape, each anchor bar comprising a distal end, configured to be inserted into a bone element, and a proximal end; and
   at least one connecting bar, corresponding to a horizontal bar of the U shape, connecting together the respective proximal ends of the two anchor bars, said connecting bar comprising at least one longitudinal opening splitting it into two opposite side walls connected together at the ends thereof, deformable in a plane P containing the connecting bar and perpendicular to a plane containing the U-shaped osteosynthesis clip, such that the longitudinal opening is adapted to assume a closed configuration, in which the two anchor bars are substantially parallel to each other and said two side walls are brought close to each other such that a distance between the two proximal ends of the two anchor bars has a value L1, and at least one open configuration, in which central regions of said two side walls are spaced apart from each other on either side of said longitudinal opening, and the distance between the two proximal ends of the two anchor bars has a value L2 strictly lower than L1;
   wherein said osteosynthesis clip further comprises a compression piece having at least one active portion, a cross-section of which in a plane A of said compression piece has an overall oval shape, said compression piece being housed within said longitudinal opening with its plane A coinciding with said plane P and at least one part of an outer face of its active portion in contact with at least one part of inner faces of said two side walls of the connecting bar, said piece being adapted to undergo a rotation about an axis B passing through the center of said oval shape of said active portion and perpendicular to said plane P, thus causing said longitudinal opening to move from its closed configuration to its open configuration, and vice versa.

2. The osteosynthesis clip according to claim 1, further comprising means for guiding the rotation of said compression piece in said plane P.

3. The osteosynthesis clip according to claim 2, wherein the guiding means comprises at least one groove and one bead adapted to engage one inside the other to guide the rotation of said compression piece in said plane P, one of said groove and said bead being located on the inner faces of said side walls, the other of said groove and said bead being located on said outer face of said active portion of said compression piece.

4. The osteosynthesis clip according to claim 1, further comprising means for blocking said compression piece at different angles of rotation.

5. The osteosynthesis clip according to claim 4, wherein said blocking means comprises a plurality of reliefs distributed along a periphery of said active portion, adapted to successively engage in one or more complementary reliefs located on the inner faces of said side walls, the engagement of one or more reliefs in the complementary relief(s) blocking said rotating piece at a determined angle of rotation.

6. The osteosynthesis clip according to claim 1, further comprising misalignment means for misaligning said anchor bars, arranged to cause the respective distal ends of said anchor bars to alternately move away from each other or get closer to each other, in an open configuration of said longitudinal opening.

7. The osteosynthesis clip according to claim 6, wherein said misalignment means comprises a longitudinal slot made in each side wall and splitting said each side wall into two longitudinal sections, a proximal section and a distal section, connected together at each end thereof, each of said proximal and distal sections being deformable in the plane P, independently of the other section.

8. The osteosynthesis clip according to claim 7, wherein said part of said outer face of said active portion of said compression piece being in contact only with the inner faces of said proximal sections of said side walls, said distal regions of said two anchor bars move away from each other when said longitudinal opening is in an open configuration.

9. The osteosynthesis clip according to claim 7, wherein said part of said outer face of said active portion of said compression piece being in contact only with the inner faces of said distal sections of said side walls, said distal regions of said two anchor bars get closer to each other when said longitudinal opening is in an open configuration.

10. The osteosynthesis clip according to claim 1, wherein the distal regions of said two anchor bars are provided with hooking notches intended to reinforce anchoring of said anchor bars into the bone elements.

11. The osteosynthesis clip according to claim 1, wherein a proximal face of said compression piece includes a surface adapted to cooperate with a tool in order to transmit a rotational movement to said compression piece.

* * * * *